United States Patent
Nagai et al.

(10) Patent No.: US 6,946,438 B1
(45) Date of Patent: Sep. 20, 2005

(54) USE OF COMPOUNDS THAT REDUCE ALPHA2-ANTIPLASMIN IN VIVO FOR THE PREPARATION OF A COMPOSITION FOR THE TREATMENT OF ISCHEMIC STROKE

(75) Inventors: Nobuo Nagai, Shizuoka (JP); Désiré José Collen, London (GB)

(73) Assignees: Desire Jose Collen (BE); Leuven Research & Development VZQ (BE)

( * ) Notice: Subject to any disclaimer, the term of this patent is extended or adjusted under 35 U.S.C. 154(b) by 0 days.

(21) Appl. No.: 09/806,178

(22) PCT Filed: Sep. 24, 1999

(86) PCT No.: PCT/EP99/07405

§ 371 (c)(1),
(2), (4) Date: Jun. 18, 2001

(87) PCT Pub. No.: WO00/18436

PCT Pub. Date: Apr. 6, 2000

(30) Foreign Application Priority Data

Sep. 29, 1998 (EP) .............................................. 98203280
Jun. 22, 1999 (EP) .............................................. 99202004

(51) Int. Cl.[7] .............................................. A61K 38/00
(52) U.S. Cl. ......................................................... 514/2
(58) Field of Search ....................... 514/2, 1; 424/130.1

(56) References Cited

FOREIGN PATENT DOCUMENTS

| EP | 0631786 | 6/1998 |
|---|---|---|
| WO | 9812329 | 3/1998 |

OTHER PUBLICATIONS

Bork (2000) "Powers and Pitfalls in Sequence Analysis: The 70% Hurdle." Genome Research 10:398–400.*

Skolnick and Fetrow (2000) "From gene to protein structure and function: novel applications of computational approaches in th genomic era." Trends in Biotech. 18(1): 34–39.*

Doerks et al., (Jun. 1998) "Protein annotation: detective work for function prediction." Trends in Genetics 14(6): 248–250.*

Smith and Zhang (Nov. 1997) "The challenges of genome sequence annotation or 'The devil is in the details'." Nature Biotechnology 15:1222–1223.*

Brenner (Apr. 1999) "Errors in genome annotation." Trends in Genetics 15(4): 132–133.*

Bork and Bairoch (Oct. 1996) "Go hunting in sequence databases but watch out for the traps." Trends in Genetics 12(10): 425–427*

(Continued)

*Primary Examiner*—Elizabeth Kemmerer
*Assistant Examiner*—Christopher James Nichols
(74) *Attorney, Agent, or Firm*—Webb Ziesenheim Logsdon Orkin & Hanson, P.C.

(57) ABSTRACT

The present invention relates to a new means for the treatment of focal ischemic cerebral infarction (ischemic stroke). It has been found that reduction of $\alpha_2$-antiplasmin leads to a significantly smaller focal cerebral infarct size. The invention therefore provides the use of compounds that reduce $\alpha_2$-antiplasmin concentration or activity in vivo, for the preparation of a therapeutic composition for the treatment of focal cerebral ischemic infarction (ischemic stroke).

1 Claim, 3 Drawing Sheets

OTHER PUBLICATIONS

Lapchak et al. (Sep. 2002) "Microplasmin: A Novel Thrombolytic That Improves Behavioral Outcome After Embolic Strokes in Rabbits." Stroke 33(9): 2279–2284.*

Bell (1997) "Evaluation of Thrombolytic Agents." Drugs 54(Supplement 3): 11–17.*

Smalling (Nov.15, 1997) "A fresh look at the molecular pharmacology of plasminogen activators: From theory to test tube to clinical outcomes." Am. J. Health–Syst. Pharm. 54(Suppl. 1): S17–S22.*

Nagai et al. (May 15, 2001) "Depletion of circulating a2–antiplasmin by intravenous plasmin or immunoneutralizt6oin reduce focal cerebral schemic injury in the absence of arterial recanalization" . Blood 97(10): 3086–3092.*

Reddy (Jan. 1998) "Newer Thrombolytic drugs for acute myocardial infarction" Indian Journal of Experimental Biology 36(1): 1–15.*

Stedman's Medical Dictionary, 2002 Physician's Desk Reference Medical Economics Company Inc.*

Rahman et al. (2001) Antifibrinolytic Effect of Single apo(a) kringle domains: Relationship to fibrinogen binding Protein Engineering 14(6): 427–438.*

Wells (1990) Additivity of Mutational Effects in Proteins Biochemistry 29(37): 8509–8517.*

Ngo et al. (1994) Coputational Complexity. Protein Structure Prediction, and the Levinthal Paradox The Protein Folding Problem and Tertiary Structure Prediction Chapter 14 pp. 433–506.*

Butte, A. et al., "Alpha2–antiplasmin causes thrombi to resist fibrinolysis induced by tissue plasminogen activator in experimental pulmonary embolism." Circulation 95(7), 1886–1891(1997).

Reed, G., "Functional characterization of monoclonal antibody inhibitors of alpha2–antiplasmin that accelerate fibrinolysis in different animal plasmas." Hybridoma 16(3):281–286 (1997).

Nagai, N.; et al., "Role of plasminogen system components in focal cerebral ischemic infarction: a gene targeting and gene transfer study in mice." Circulation 99(18):2440–2444(1999).

Collen, D. "Staphylokinase: a potent, uniquely fibrin–selective thrombolytic agent." Nature Medicine 4(3): 279–284 (1998).

Coyle. J. T. et al. "Oxidative stress, glutamate and neurodegenerative disorders," Science 262: 689–695 (1993).

Coyle. J. T. et al. "In situ injection of kainic acid: a new method for selectively lesioning neuronal cell bodies while sparing axons of passage" J Comp Neurol 180:301–323 (1978).

Tsirka, S.E. et al. "Excitotoxin–induced neuronal degeneration and seizure are mediated by tissue plasminogen activator." Nature377: 340–344(1995).

Tsirka. S.E. et al. "An extracellular proteolytic cascade promotes neuronal degeneration in the mouse hippocampus." J Neurosci 17(2):543–552 (1997).

Tsirka S.E. et al. "Neuronal cell death and t–PA," Nature 384: 123–124 (1996).

Chen, Z.L. et al. "Neuronal death in the hippocampus is promoted by plasmin–catalyzed degradation of laminin." Cell 91:917–925 (1997).

Wang. Y.F. et al. "Tissue plasminogen activator (tPA) increases neuronal damage after focal cerebral ischemia in wild–type and tPa–deficient mice." Nature Medicine 4(2): 228–231(1998).

Nagai, N. et al. "Comparative effects of tissue–type plasminogen activator, streptokinase, and staphylokinase on cerebral ischemic infarction and pulmonary clot lysis in hamster models," Circulation 100: 2541–2546 (1999).

The National Institute of Neurological Disorders and Stroke rt–Pa Stroke Study Group "Tissue plasminogen activator for acute ischemic stroke." N Engl J Med 333(24): 1581–1587 (1995).

Hacke, W. et al. for the ECASS Study Group "Intravenous thrombolysis with recombinant tissue plasminogen activation for acute hemispheric stroke: the European Cooperative Acute Stroke Sudy (ECASS)," J Am Med Ass 274(13):1017–1025 (1995).

Collen, D. et al "Turnover of antiplasmin, the fast–acting plasmin inhibitor of plasma," Blood 53(2):313–324 (1979).

Carmeliet P. et al. "Physiological consequences of loss of plasminogen activator gene function in mice," Nature 368: 419–424 (1994).

Carmeliet, P. et al. "Plasminogen activator inhibitor–1 gene–deficient mice: I. Generalization by homologous recombination and characterization," J Clin Invest 92:2746–2755 (1993).

Carmeliet, P. et al. "Plasminogen activator inhibitor–1 gene deficent mice: II. Effects on hemostatis, thrombosis and, thrombolysis," J Clin Invest 92:2756–2760 (1993).

Ploplis, V.A. et al. "Effects of disruption of the plasminogen gene on thrombosis, growth, and health in mice," Circulation 92(9): 2585–2593 (1995).

Lijnen, H.R. et al. "Alpha2–antiplasmin gene–deficiency in mice is associated with enhanced fibrinolytic potential without overt bleeding," Blood 93(7):2274–2281 (1999).

Dewerchin, M. et al. "Generation and characterization of urokinase receptor–deficient mice," J Clin Invest 97(3):870–878 (1996).

Lijnen, H. R. et al. "Amino–acid sequence of human Alpha2–antiplasmin," Eur J Biochem 166:565–574 (1987).

McGrory, W.J. et al. "A simple technique for the rescue of early region 1 mutations into infectious human adenovirus type 5." Virology 163:614–617 (1988).

Gomez–Foix, A.M. et al. "Adenovirus–mediated transfer of the muscle glycogen phosphorylase gene into hepatocytes confers altered regulation of glycogen metabolism," J Biol Chem 267(35):25129–25134 (1992).

Graham, F.L. et al. "Characteristics of a human cell line transformed by DNA from human adenovirus type 5," J Gen Virol 36: 59–72 (1977).

Gerard, R.D., Meidel, R.S. "Adenovirus vectors. In: Hames, B.D., Glover, D. (eds.) DNA Cloning 4—A practical approach: mammalian systems," Oxford, UK, pp. 285–306 (1995).

Alcorn, J.L. et al. "Genomic elements involved in transcriptional regulation of the rabbit surfactant protein–A gene," Mol Endocrinol 7(8): 1072–1085 (1993).

Kopler, W.P. et al. "Adenovirus–mediated transfer of gene encoding human apolipoprotein A–I into normal mice increases circulating high–density lipoprotein cholesterol." Circulation 90(3): 1319–1327 (1994).

Carmeliet, P. et al. "Adenovirus–mediated transfer of tissue–type plasminogen activator augments thrombolysis in tissue–type plasminogen activator–deficient and plasminogen activator inhibitor–1–overexpressing mice," *Blood* 90(4): 1527–1534 (1997).

Carmeliet, P. et al. "Inhibitory role of plasminogen activator inhibitor–1 in arterial wound healing and neointima formation," *Circulation* 96(9): 3180–3191 (1997).

Deutsch, D.G. et al. "Plasminogen purification from human plasma by affinity chromatography," *Science* 170: 1095–1096 (1970).

Edy, J. et al. "Inhibition of plasmin by normal and antiplasmin–depleted human plasma." *Thromb. Res.* 8: 513–518 (1976).

Welsh, F.A. et al. "Effect of lactacidosis on pyridine nucleotide stability during ischemia in mouse brain," *J Neurochem* 49(3): 846–851 (1987).

Bederson, J.B. et al., "Rat middle cerebral artery occlusion: evaluation of the model and development of a neurologic examination," *Stroke* 17(3): 472–476 (1986).

Bederson, J.B. et al. "Evaluation of 2,3,5–triphenyltetrazolium chloride as a stain for detection and quantification of Experimental cerebral infarction in rats," *Stroke* 17(6): 1304–1308 (1986).

* cited by examiner

USE OF COMPOUNDS THAT REDUCE ALPHA2-ANTIPLASMIN IN VIVO FOR THE PREPARATION OF A COMPOSITION FOR THE TREATMENT OF ISCHEMIC STROKE

BACKGROUND OF THE INVENTION

1. Field of the Invention

The present invention relates to a new means for the treatment of focal ischemic cerebral infarction ischemic stroke.

2. Description of the Related Art

Focal ischemic cerebral infarction occurs when the arterial blood flow to a specific region of the brain is reduced below a critical level resulting in neuronal cell death. It is thought that neuronal degeneration in central nervous system (CNS) diseases such as stroke, epilepsy and Alzheimer's disease is stimulated by an excess of the excitatory amino acid glutamate (2). Injection of glutamate agonists in the CNS indeed induces hippocampal neuronal cell death similar to that observed in neurodegenerative diseases (3).

Excitotoxin-induced neuronal degeneration is mediated by tissue-type plasminogen activator (t-PA) (4). Consistent with this observation, mice deficient in t-PA are resistant to, and infusion of plasminogen activator inhibitor-1 (PAI-1) protects against excitotoxin-mediated hippocampal neuronal degeneration (4-6).

Furthermore, deficiency of plasminogen (Plg), the zymogen substrate of t-PA, and infusion of $\alpha_2$-antiplasmin ($\alpha_2$-AP), protect mice against excitotoxin-induced hippocampal neuronal death (5). It has been proposed that plasmin-mediated degradation of laminin sensitizes hippocampal neurons to cell death by disrupting neuron-extracellular matrix interaction (7).

Wang et al. (8) recently demonstrated that neuronal damage after focal cerebral ischemia induced by transient occlusion of the middle cerebral artery was also reduced in mice with t-PA deficiency and exacerbated by t-PA infusion. This suggests that the plasminogen system may be involved both in establishing a cerebral ischemic infarct and in its extension during thrombolytic therapy. It was recently demonstrated that the neurotoxic effect of t-PA on persistent focal cerebral ischemia also occurred with other thrombolytic agents, including streptokinase and staphylokinase (9). Thus, in those patients with persistent cerebral arterial occlusion, thrombolytic therapy for ischemic stroke may cause infarct extension, which would not only partially offset the established overall beneficial effect of arterial recanalization (10, 11), but indeed be harmful to a subgroup of patients. Because it is not possible to distinguish between patients who will and those who will not achieve cerebral arterial recanalization with thrombolytic therapy, the development of specific conjunctive strategies to counteract the neurotoxic effects of thrombolytic agents on persisting focal cerebral ischemia appear to be warranted.

SUMMARY OF THE INVENTION

The invention relates to a new means for treating ischemic stroke. It is an object of this invention to treat focal cerebral ischemic infarction by administering at least one compound that reduces $\alpha_2$-antiplasmin in vivo in the form of a therapeutical composition, so that the size of the focal cerebral ischemic infarct is reduced. Compounds of the invention reducing $\alpha_2$-antiplasmin concentration or activity are, for example, plasmin, mini-plasmin (lacking the first four kringles) and micro-plasmin (lacking all five kringles). Also suitable for reducing $\alpha_2$-antiplasmin concentration or activity are neutralizing antibodies, such as monoclonal antibodies, and derivatives of neutralizing antibodies, such as Fab fragments and scFv fragments.

DESCRIPTION OF THE PREFERRED EMBODIMENTS

It is therefore the object of the present invention to provide a new means for treating ischemic stroke.

In the research that led to the present invention the following was contemplated. Although it is assumed that neuronal injury during focal ischemia in the brain occurs primarily as a result of accumulation of excitotoxins such as glutamates, the role of plasmin-mediated laminin degradation or alternative mechanisms in the pathogenesis of cortical neuronal cell death has not been demonstrated. In order to delineate the contribution of individual components of the plasminogen (fibrinolytic) system on focal cerebral ischemic infarction, the present inventors then quantitated infarct size produced by ligation of the left middle cerebral artery (MCA) in mice with targeted inactivation of the genes encoding Plg, its activators tissue-type plasminogen activator (t-PA) or urokinase-type plasminogen activator (u-PA), or the fibrinolytic inhibitors PAI-1 or $\alpha_2$-AP. In addition, the effects of adenoviral transfer of the t-PA and PAI-1 genes and of infusion of human $\alpha_2$-AP on cerebral infarction were studied.

Whereas the findings of Strickland et al., that t-PA deficiency protects against focal cerebral ischemic infarction were fully confirmed, and extended by the observation that PAI-1 deficiency resulted in significantly larger infarct sizes, the observation that Plg deficiency protects against excitotoxin induced neuronal cell death could not be confirmed. Instead it was found that focal cerebral infarct size was significantly larger in mice with Plg deficiency and conversely, significantly smaller in mice with $\alpha_2$-AP deficiency.

In aggregate, these findings indicate that plasminogen system components affect focal cerebral ischemic infarct size at two different levels: 1) reduction of t-PA activity (t-PA gene inactivation or PAI-1 gene transfer) reduces, while its augmentation (t-PA gene transfer or PAI-1 gene inactivation) increases infarct size, and 2) reduction of Plg activity (Plg gene inactivation or $\alpha_2$-AP injection) increases, while its augmentation ($\alpha_2$-AP gene inactivation or $\alpha_2$-AP neutralization) reduces infarct size. The findings are incompatible with a unique linked pathway in which t-PA-mediated plasmin generation would lead to neuronal cell death, but suggests two independent (t-PA mediated and Plg-mediated, respectively) mechanisms operating in opposite direction.

The internally consistent observations with $\alpha_2$-AP were unexpected but are most relevant for the treatment of ischemic stroke. Firstly a correlation was found between infarct size and genotype with heterozygotes displaying infarct sizes between those of the wild type and homozygous phenotypes. Secondly, bolus injection of human $\alpha_2$-AP (h$\alpha_2$-AP) in $\alpha_2$-AP$^{-/-}$ mice caused a dose-related infarct expansion. Importantly, Fab fragments from affino-specific polyclonal rabbit anti-h$\alpha_2$-AP antibodies, given intravenously 40 min after occlusion of the MCA, significantly reduced the cerebral ischemic infarct size. This observation suggests a potential avenue to counteract focal ischemic infarction with the use of $\alpha_2$-AP inhibitors (e.g. neutralizing monoclonal antibodies or compounds neutralizing $\alpha_2$-AP activity). This approach was confirmed by infusion of plasmin in mice with MCA occlusion which, by neutralizing $\alpha_2$-AP, significantly reduced infarct size. The concentration of $\alpha_2$-AP in human plasma is 1 mM (12), corresponding to a total body pool of approximately 500 mg. An equivalent dose of a monoclonal Fab fragment would be approximately 400 mg, and that of plasmin approximately 500 mg, which is high but not excessive for single therapeutic administration. Furthermore, the observation that infarct size is proportional to the $\alpha_2$-AP level (derived from the gene dose effect and the dose-response) suggests that a partial reduction of the plasma level might have a significant beneficial effect.

In view of the above the invention thus relates is to the use of compounds that reduce $\alpha_2$-AP activity in vivo for the treatment of focal cerebral ischemic infarction (ischemic stroke).

In a specific embodiment of the invention use is made of compounds that reduce the circulating $\alpha_2$-AP concentration. A lower concentration of $\alpha_2$-AP will lead to a lower activity. In an alternative embodiment, the activity of circulating $\alpha_2$-AP is reduced directly.

Compounds that are suitable for the reduction of $\alpha_2$-AP concentration and activity are for example $\alpha_2$-AP neutralizing antibodies or derivatives thereof. Preferred antibodies are monoclonal antibodies. Derivatives are preferably Fab fragments, scFv fragments.

Compounds neutralizing $\alpha_2$-AP are for example plasmin, mini-plasmin (lacking the first 4 kringles) or micro-plasmin (lacking all five kringles).

Figure 1:
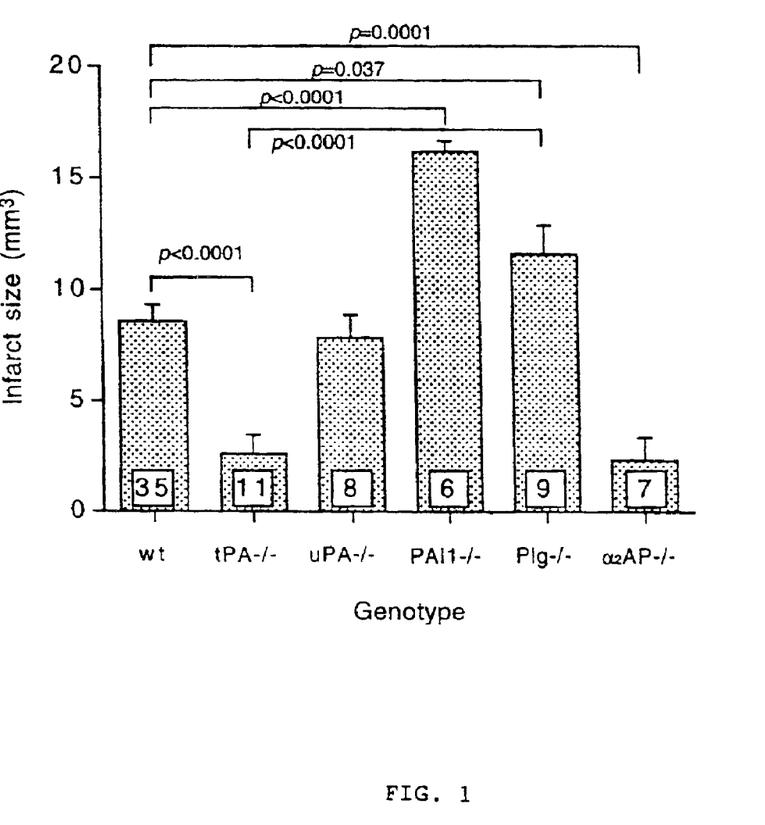
FIG. 1 is a graph of infarct volume plotted relative to amounts of plasminogen system components.
Figure 2A:
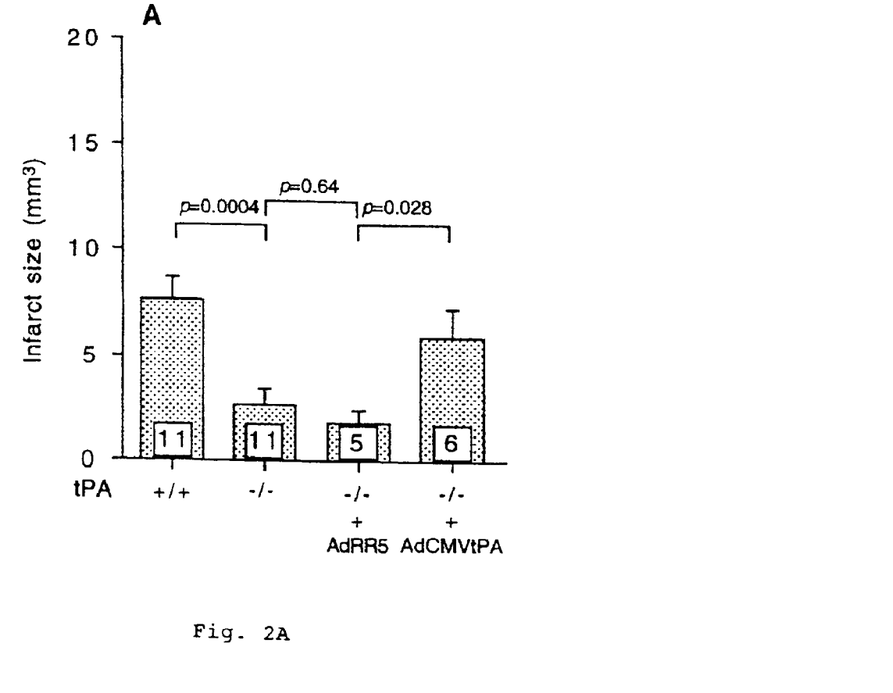
FIG. 2 is a graph of infarct volume plotted relative to adenoviral transfer of t-PA or PAI-1 genes.
Figure 2B:
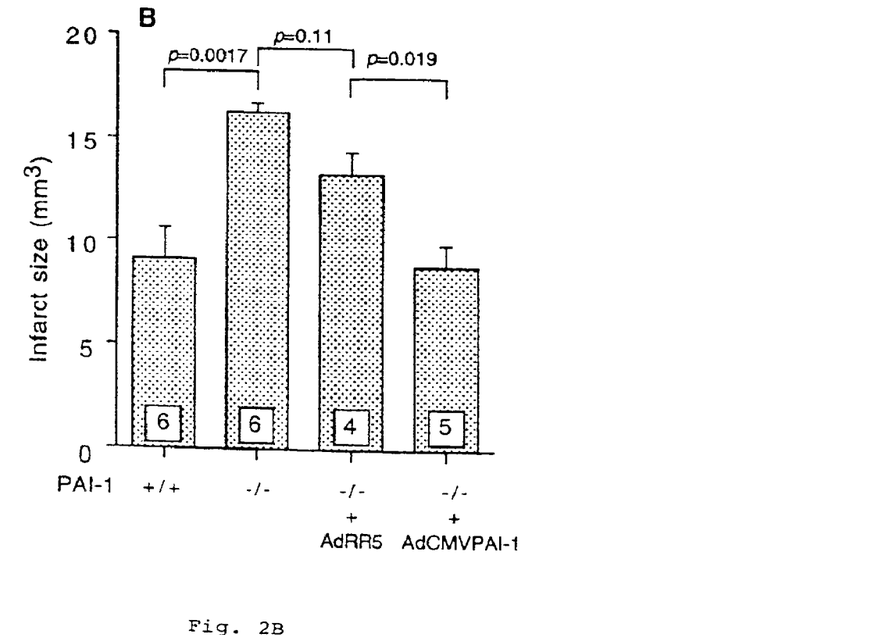
Figure 3A:
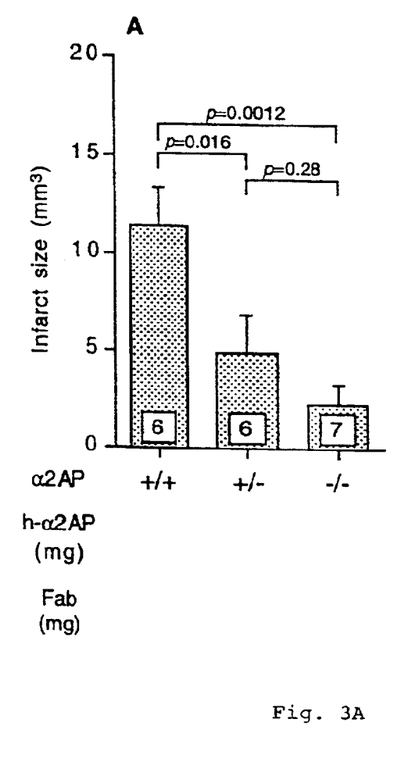
FIG. 3 is a graph of infarct volume plotted relative to (A) $\alpha_2$-AP genotype and (B) injection of h$\alpha_2$-AP or of h$\alpha\alpha_2$-AP followed by anti-h$\alpha_2$-AP fragments.
Figure 3B:
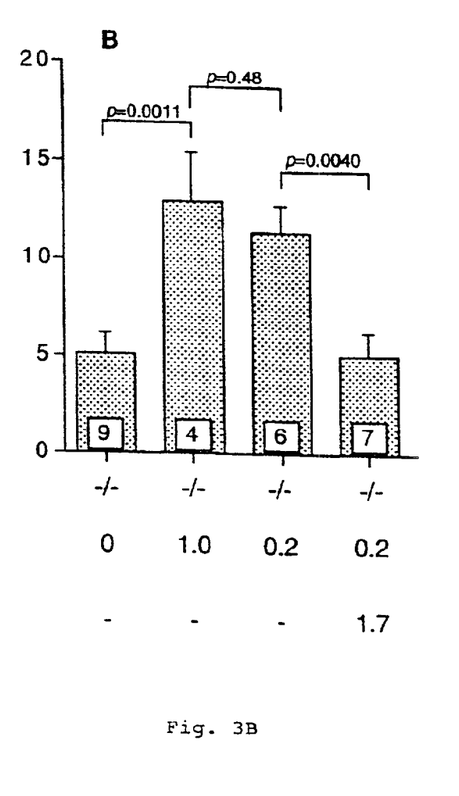

The present invention will be demonstrated in more detail in the following examples, which are however not intended to be limiting to the scope of the invention. In the examples reference is made to the following drawings:

FIGS. 1 to 3 are histograms comparing the volume (in mm$^3$) of focal cerebral ischemic infarcts after ligation of the middle cerebral artery (MCA) in mice. The data represent mean values and the vertical bars SEM, with the number of experiments given in the columns.

FIG. 1 shows the effect of deficiency of plasminogen system components (genotype in abscissa) on focal ischemic cerebral infarct size (in mm$^3$).
WT: wild type (pooled values of 50% C57BL6/50% S129, 100% C57BL6 and 100% S129 genetic background).

FIG. 2A shows the effect of adenoviral transfer of the t-PA gene on focal ischemic cerebral infarct size in t-PA deficient mice.

FIG. 2B shows the effect of adenoviral transfer of the PAI-1 gene on focal ischemic cerebral infarct size in PAI-1 deficient mice.

FIG. 3 shows the effect of $\alpha_2$-AP on focal ischemic cerebral infarct size.

A. Effect of $\alpha_2$-AP genotype on cerebral infarct size.

B. Effect of injection of h$\alpha_2$-AP or of h$\alpha\alpha$-AP followed by anti-h$\alpha_2$-AP Fab fragments on cerebral infarct size.

EXAMPLES

Example 1

Murine Cerebral Ischemic Infarction Model

1. Introduction

All mice included in the present study were generated and bred at the Specific Pathogen Free Facility of the Center for Transgene Technology and Gene Therapy, Campus Gasthuisberg, K. U. Leuven. Gene inactivation was obtained by homologous recombination in embryonic stem cells targeting the genes encoding tissue-type plasminogen activator (t-PA) (13), urokinase-type plasminogen activator (u-PA) (13), plasminogen activator inhibitor-1 (PAI-1) (14, 15), plasminogen (Plg) (16), or $\alpha_2$-antiplasmin ($\alpha_2$-AP) (17), as previously described. Mice with inactivated genes encoding u-PA receptor (u-PAR) (18) were not included because of the normal results obtained with u-PA deficient mice.

2. Materials and Methods 2.1 Materials

Human $\alpha_2$-AP was prepared from fresh frozen plasma as previously described (19).

Polyclonal antisera were raised in rabbits by subcutaneous injection of 200 mg purified human $\alpha_2$-AP suspended in complete Freund's adjuvant, followed at two biweekly intervals by injection of the antigen suspended in incomplete Freund's adjuvant. Serum was obtained by repeated ear vein puncture. Pooled sera were chromatographed on Protein-A Sepharose (0.5 ml serum per ml wet gel), equilibrated with 0.1 M Tris.HCl, pH 8.1 and IgG eluted with 0.1 M glycine.HCl, pH 2.8, yielding approximately 10 mg protein per ml serum. Affino-specific antibodies were obtained from the dialyzed IgG pool by chromatography on a CNBr-activated Sepharose column substituted with human $\alpha_2$-AP (2.5 mg/ml wet gel) and eluted with 0.1 M glycine.HCl, pH 2.8, yielding approximately 0.1 mg specific IgG per mg applied.

Fab fragments were obtained from the affino-specific IgG by digestion with papain. Therefore IgG was dissolved to a concentration of 5 mg/ml and digested with 1 percent (w/w) papain in the presence of 50 mM cysteine, 1 mM EDTA, 0.1 M phosphate buffer, pH 7.0 for 5 hours. The reaction was arrested by addition of iodoacetamide to a final concentration of 75 mM. After dialysis the mixture was purified on a protein A Sepharose column equilibrated with PBS. Fab concentration was determined by ELISA calibrated against an IgG standard. SDS gel electrophoresis essentially revealed homogeneous Fab fragments (not shown).

2.2 Production of Adenoviral Vectors

The recombinant adenoviruses AdCMVt-PA and AdCMVPAI-1 were generated by homologous recombination in 293 cells essentially as previously described (20). For AdCMVt-PA, an XbaI-fragment of the plasmid pSTEt-PA encoding wild type human t-PA was ligated into XbaI-digested pACCMVpLpA (21) to produce pACCMVt-PA. The adenovirus precursor pACCMVPAI-1 was generated by ligating the 1.4-kb EcORI/BglII fragment of pPAI-1RBR containing the entire coding sequence of human PAI-1 into EcORI/BamHI-digested pACCMVpLpA. In these plasmids, the t-PA and PAI-1 cDNA are positioned between the human cytomegalovirus immediate-early enhancer/promoter and the SV40 t-antigen intron/polyadenylation signal to form a complete transcriptional unit.

Monolayer cultures of 293 cells (22) were cotransfected with 10 mg of pACCMVt-PA or pACCMVPAI-1 and 5 mg of pJM17 (20), a plasmid containing a full-length adenovirus 5 dl309 genome. Homologous recombination between these plasmids results in the formation of recombinant viral genomes in which the adenovirus E1 region is replaced by the respective t-PA or PAI-1 transgenes. Replication of the recombinant viruses in cultured 293 cells is supported by E1A gene products supplied in trans from a copy of E1 integrated into the 293 cell genome.

After transfection, recombinant viral plaques were harvested and amplified as described (23). The identity of recombinant viruses was determined by restriction analysis and Southern blotting of viral DNA prepared from productively infected 293 cells. The recombinant adenovirus AdRR5, which lacks an inserted gene in the E1 position, was generated from pACRR5 and pJM17 in the same manner and was used as a control adenovirus (24, 25). Recombinant viruses were replaqued to ensure clonal identity before further use. Large scale production of recombinant adenovirus was performed as described (23). Purified virus was supplemented with 0.1 mg/ml sterile bovine serum albumin (BSA), snap frozen in liquid nitrogen and stored at −80° C. until use. The titer of infectious viral particles in purified stocks was determined by plaque assay on monolayers of 293 cells with 1 hour of adsorption at 37° C. Purified viral stocks of $>10^{10}$ plaque forming units (pfu) per ml were routinely obtained. The kinetics and organ distribution of t-PA and PAI-1 expression following adenoviral transfer by intravenous bolus injection have been described elsewhere (26, 27).

2.3 Preparation of Human Plasmin

Human plasminogen was prepared from fresh frozen human blood bank plasma, essentially as described previously (28). Human plasma (6 liter), to which 20 units aprotinin (Trasylol, Bayer, Germany) was added per ml, was cleared by centrifugation at 4,000 rpm for 15 min at 4° C. Lysine-Sepharose (200 g wet weight, substitution level approximately 1 mg lysine per g wet Sepharose gel) was added to the supernatant, the mixture stirred for 1 hour at 4° C. and the gel recovered on a Buchner funnel. Then 120 g Lysine-Sepharose was added to the filtrate, the mixture stirred and the gel recovered as above. The combined gel fractions were washed with 18 liter 0.2 M $K_2HPO_4/KH_2PO_4$ buffer, pH 7.5, containing 10 units aprotinin per ml, then poured into a 5×60 cm column and washed with 0.02 M $NaH_2PO_4$, 0.1 M NaCl buffer, pH 7.5, containing 10 units/ml aprotinin at 4° C. until the absorbance of the wash fluid at 280 nm was less than 0.05. The column was then eluted with wash buffer containing 0.05 M 625 aminohexanoic acid and protein containing fractions pooled. From 6 liter plasma approximately 145 ml fluid containing 650 mg protein was obtained. The pool was concentrated 2.5-fold on an Amicon PM10 filter and gel filtered on a 5×90 cm column of ultragel AcA44 equilibrated with 0.02 M $NaH_2PO_4$, 0.1 M NaCl buffer, pH 7.5, at a rate of 60 ml per hour. The main peak, containing approximately 590 mg protein was concentrated on an Amicon PM10 filter to a concentration of 10 mg/ml and frozen until use.

Human plasmin was prepared from plasminogen as follows. Lysine-Sepharose (20 g wet gel) was added to human plasminogen (200 mg) solution, the mixture stirred for 3 hours at 4° C., the gel washed on a Buchner funnel and resuspended in 30 ml 0.1 M $NaH_2PO_4$ buffer, pH 7.4. Urokinase (500 µl of a 50 µM solution, prepared by activation of Saruplase (Grünenthal, Aachen, Germany) with Plasmin.Sepharose was added and the mixture stirred for 15 hours at 4° C. The gel was then washed on a Buchner funnel with 0.1 M $NaH_2PO_4$ buffer, pH 7.4, poured into a 1.5×16 cm column, washed with 0.1 M $NaH_2PO_4$ buffer, pH 7.4 until the absorbance at 280 nm of the wash fluid was less than 0.05, and eluted with 0.1 M $NaH_2PO_4$ buffer containing 0.05 M 6-aminohexanoic acid. The protein containing fractions were pooled, glycerol was added to a final concentration of 10 percent and the pool was dialyzed at 4° C. against 0.1 M $NaH_2PO_4$ buffer containing 10 percent glycerol. The final recovery was 25 ml solution with a protein concentration of 4.0 mg/ml and an active plasmin concentration of 25 µM.

2.4 Measurement of $\alpha_2$-Antiplasmin in Plasma $\alpha_2$-Antiplasmin levels in murine plasma were measured by a chromogenic substrate assay, based on its rapid inhibition of plasmin (29). Briefly 10 µl mouse plasma (diluted ¹⁄₁₀ in 0.05 M $NaH_2PO$, buffer, pH 7.4, containing 0.01% Tween 20) is mixed at 37° C. with 420 µl 0.05 Tris HCl, 0.1 M NaCl buffer, pH 7.4, containing 0.01% Tween 20, and with 20 µl of 0.125 µM human plasmin (final concentration 5 nM). After 10 s incubation, 50 µl of 3 mM S2403 (Chromogenics, Antwerp, Belgium) is added and the change in absorbance measured at 405 nm. The change in absorbance is approximately 0.18 $min^{-1}$ with buffer and 0.09 $min^{-1}$ with pooled murine plasma.

2.5 Animal Experiments

Animal experiments were conducted according to the guiding principles of the American Physiological Society and the International Committee on Thrombosis and Haemostasis (30).

Focal cerebral ischemia was produced by persistent occlusion of the MCA according to Welsh et al. (31). Briefly, mice of either sex, weighing 20 to 30 g, were anesthetized by intraperitoneal injection of ketamine (75 mg/ml, Apharmo, Arnhem, The Netherlands) and xylazine (5 mg/ml, Bayer, Leverkusen, Germany). Atropine (1 mg/kg; Federa, Brussels, Belgium) was administered intramuscularly, and body temperature was maintained by keeping the animals on a heating pad. A "U" shape incision was made between the left ear and left eye. The top and backside segments of the temporal muscle were transsected and the skull was exposed by retraction of the temporal muscle. A small opening (1 to 2 mm diameter) was made in the region over the MCA with a hand-held drill, with saline superfusion to prevent heat injury. The meningae were removed with a forceps and the MCA was occluded by ligation with 10-0 nylon thread (Ethylon, Neuilly, France) and transsected distally to the ligation point. Finally, the temporal muscle and skin were sutured back in place.

AdCMVt-PA, AdCMVPAI-1 or AdRR5 were given as an intravenous bolus of 1.3×10⁹ plaque forming units (p.f.u.) 4 days before ligation of the MCA. Human $\alpha_2$-AP (h$\alpha_2$-AP) was given intravenously divided in 2 injections, given 1 min before and 30 min after ligation of the MCA, respectively. Fab fragments were injected intravenously as a bolus, 10 min after the second h$\alpha_2$-AP injection. Human plasmin was given intravenously as a bolus, either 15 min before or 15 min after ligation of the MCA.

The animals were allowed to recover and were then returned to their cages. After 24 hours, the animals were sacrificed with an overdose of Nembutal (500 mg/kg, Abbott Laboratories, North Chicago, Ill.) and decapitated. The brain was removed and placed in a matrix for sectioning in 1 mm segments. The sections were immersed in 2% 2,3,5-triphenyltetrazolium chloride (TTC) in saline (32), incubated for 30 min at 37° C., and placed in 4% formalin in phosphate buffered saline. With this procedure, the necrotic infarct area remains unstained (white) and is clearly distinguishable from stained (brick red) viable tissue. The sections were photographed and subjected to planimetry. The infarct volume was defined as the sum of the unstained areas of the sections multiplied with their thickness.

The data are represented as mean±SEM of n determinations. The significance of differences was determined using analysis of variance followed by Fisher's PLSD test, using the Statview software package or by Student's t-test.

Example 2
Cerebral Ischemic Infarct Size in Mice with Targeted Inactivation of Genes Encoding Plasminogen System Components Ligation of the left MCA induced a cerebral infarct with a volume of 7.6±1.1 mm$^3$ (n=11) in wild type mice with a mixed (50%) S129 and (50%) C57BL/6 genetic background, of 9.3±2.7 mm$^3$ (n=6) in inbred C57BL/6 mice and of 6.4±1.3 mm$^3$ (n=6) in inbred S129 mice (p=NS versus mixed background, results not shown).

Inactivation of the t-PA gene was associated with a significant reduction of infarct size to 2.6±0.80 mm$^3$ (n=11), (p<0.0001 vs wild type mice), whereas inactivation of the u-PA gene had no effect on infarct size (7.8±1.0 mm$^3$, n=8, p=NS vs wild type).

Inactivation of the PAI-1 gene was associated with a significant increase in infarct size (16±0.52 mm$^3$, n=6, p<0.0001 vs wild type) (FIG. 1). In mice with inactivated Plg genes, cerebral infarct size was significantly larger than in wild type mice (12±1.2 mm$^3$, n=9, p=0.037 vs wild type)., whereas, conversely, in $\alpha_2$-AP gene deficient mice, infarct size was markedly reduced (2.2±1.1 mm$^3$, n=7, p=0.0001 vs wild type) (FIG. 1).

Example 3
Effect of t-PA and PAI-1 Gene Transfer on Cerebral Infarct Size

Injection of 1.3×10$^9$ p.f.u. of AdCMVt-PA in 6 t-PA$^{-/-}$ mice 4 days before MCA ligation was associated with a cerebral infarct size of 6.0±1.3 Mm$^3$, significantly larger than the infarcts in 5 t-PA$^{-/-}$ mice injected with the control virus AdRRS (1.8±0.63, p=0.028) (FIG. 2A). Conversely, injection of 1.3×10$^9$ p.f.u. of AdCMVP-AI-1 in 5 PAI-1$^{-/-}$ mice was associated with a cerebral infarct size of 10±1.4 mm$^3$, significantly smaller than the infarcts in 5 PAI-1$^{-/-}$ mice injected with the control virus ALRR5 (13±1.0 mm$^3$, pa 0.019) (FIG. 2B).

Example 4
Effect of $\alpha_2$-Antiplasmin on Cerebral Infarct Size

Cerebral infarct size correlated with $\alpha_2$-AP gene dose, corresponding to 11±2.0, 4.9±2.0 and 2.2±1.1 mm$^3$ in wild type, heterozygous and homozygous deficient mice, respectively (FIG. 3A). Injection of human $\alpha_2$-AP in groups of 4 $\alpha_2$-AP$^{-/-}$ mice increased the infarct size to 13±2.5 mm$^3$ (n=4) with a 1 mg total dose and to 11±1.5 mm$^3$ (n=6) with a 0.2 mg total dose. Injection of 1.7 mg affino-specific Fab against human $\alpha_2$-AP in mice given 0.2 mg human $\alpha_2$-AP reduced the cerebral infarct size to 5.1±1.1 mM$^3$ (n=7, pa 0.0040 vs 0.2 mg human $\alpha_2$-AP) (FIG. 3B).

The above examples show that reduction of $\alpha_2$-AP activity (reduced $\alpha_2$-AP gene expression or reduction of circulating $\alpha_2$-AP with inhibitors) reduces focal cerebral ischemic infarct size, such as encountered during ischemic stroke.

Example 5
Effect of Plasmin on Cerebral Infarct Size

Injection of 50, 100 or 150 µg human plasmin (Pli) in mice weighing approximately 30 g decreased the $\alpha_2$-AP levels in blood samples taken after 30 s to 67, 40 and 31 percent of baseline, respectively (mean of 2 mice, with less than 15 percent variability). Injection of 200 µg Pli in 3 mice reduced the plasma $\alpha_2$-AP levels to 59±4.8, 67±4.4 and 70±2.5 percent after 2, 4 and 6 hours respectively.

Ligation of the left middle cerebral artery (MCA) induced a cerebral infarct with a volume of 27±1.3 mm$^3$ (n=10) in inbred Balb/c mice, and of 16±1.3 mm$^3$ (n=12) in inbred C57BL/6 mice.

Injection of 0.2 mg Pli in Balb/c mice reduced the infarct size to 22±1.0 mm$^3$ (n=9) (p=0.006 vs saline). Similar decreases were observed when the Pli injection was given 15 min before or 15 min after ligation of the MCA (Table 1). In C57Bl/6 mice, injection of 0.2 mg Pli reduced the infarct size to 10±1.2 mm$^3$ (n=12) (p=0.004 vs saline).

REFERENCES

1. Collen D. Staphylokinase: a potent, uniquely fibrin-selective thrombolytic agent. Nature Medicine 1998; 4: 279–284.
2. Coyle J T, Puttfarcken P. Oxidative stress, glutamate and neurodegenerative disorders. Science 1993; 262: 689–695.
3. Coyle J T, Molliver M E, Kuhar M J. In situ injection of kainic acid: a new method for selectively lesioning neuronal cell bodies while sparing axons of passage. J Comp Neurol 1978; 180: 301–323.
4. Tsirka S, Gualandris A, Amaral D G, Strickland S. Excitotoxin induced neuronal degeneration and seizure are mediated by tissue plasminogen activator. Nature 1995; 377: 340–344.
5. Tsirka S, Rogove A D, Bugge T H, Degen J L, Strickland S. An extracellular proteolytic cascade promotes neuronal degeneration in the mouse hippocampus. J Neurosci 1997; 17: 543–552.
6. Tsirka S, Rogove A D, Strickland S. Neuronal cell death and t-PA. Nature 1996; 384: 123–124.
7. Chen ZL, Strickland S. Neuronal death in the hippocampus is promoted by plasmin-catalyzed degradation of laminin. Cell 1997; 91: 917–925.
8. Wang Y F, Tsirka S E, Strickland S, Stieg P E, Soriano S G, Lipton S A. Tissue plasminogen activator (t-PA) increases neuronal damage after focal cerebral ischemia in wild-type and tPA-deficient mice. Nature Medicine 1998; 4: 228–231.
9. Nagai N, Vanlinthout I, Collen D. Comparative effects of tissue-type plasminogen activator, streptokinase and staphylokinase on cerebral ischemic infarction and pulmonary clot lysis in hamster models. Submitted.
10. The National Institute of Neurological Disorders and Stroke rt-PA Stroke Study Group. Tissue plasminogen activator for acute ischemic stroke. N Engl J Med 1995; 333: 1581–1587.
11. Hacke W, Kaste M, Fieschi C, Toni D, Lesaffre E, von Kummer R, Boysen G, Bluhmki E, Haxter G, Mahagne MH, Hennerici M, for the ECASS Study Group. Intravenous thrombolysis with recombinant tissue plasminogen activator for acute hemispheric stroke: the European Cooperative Actue Stroke Study (ECASS). J Am Med Ass 1995; 274: 1017–1025.
12. Collen D, Wiman B. Turnover of antiplasmin, the fast-acting plasmin inhibitor of plasma. Blood 1979; 53: 313–324.
13. Carmeliet P, Schoonjans L, Kieckens L, Ream B, Degen J, Bronson R, De Vos R, van den Oord J, Collen D, Mulligan R. Physiological consequences of loss of plasminogen activator gene function in mice. Nature 1994; 368: 419–424.
14. Carmeliet P, Kieckens L, Schoonjans L, Ream B. van Nuffelen A, Prendergast G, Cole M, Bronson R, Collen D, Mulligan R C. Plasminogen activator inhibitor-1 gene-deficient mice. I. Generation by homologous recombination and characterization. J Clin Invest 1993; 92: 2746–2755.
15. Carmeliet P, Stassen J M, Schoonjans L, Ream B. Van den Oord J J, De Mol M, Mulligan R C, Collen D. Plasminogen activator inhibitor-1 deficient mice. II. Effects on hemostasis, thrombosis and thrombolysis. J Clin Invest 1993; 92: 2756–2760.
16. Poplis V A, Carmeliet P, Vazirzadeh S, Van Vlaenderen I; Moons L, Plow E F, Collen D. Effects of disruption of the plasminogen gene on thrombosis, growth and health in mice. Circulation 1995; 92:2585–2593.
17. Lijnen H R, Okada K, Matsuo O, Collen D, Dewerchin M. $\alpha_2$-antiplasmin gene-deficiency in mice is associated with enhanced fibrinolytic potential without overt bleeding. Blood 1999; 93:2274–2281.
18. Dewerchin M, Van Nuffelen A, Wallays G, Bouché A, Moons L, Carmeliet P. Mulligan R C, Collen D. Generation and characterization of urokinase receptor-deficient mice. J Clin Invest 1996; 97: 870–878.
19. Lijnen H R, Holmes W E, Van Hoef B, Wiman B, Rodriguez H, Collen D. Amino-acid sequence of human $\alpha_2$-antiplasmin. Eur J Biochem 1987; 166: 565–574.
20. McGrory W J, Bautista D S, Graham F L. A simple technique for the rescue of early region 1 mutations into infectious human adenovirus type 5. Virology 1988; 163: 614–617.
21. Gomez-Foix A M, Coats W S, Baque S, Alam T, Gerard R D, Newgard C B. Adenovirus-mediated transfer of the muscle glycogen phosphorylase gene into hepatocytes confers altered regulation of glycogen metabolism. J Biol Chem 1992; 267: 25129–25134.
22. Graham F L, Smiley J, Russel W C, Nairn R. Characteristics of a human cell line transformed by DNA from human adenovirus type 5. J Gen Virol 1977; 36: 59–74.
23. Gerard R D, Meidell R S. Adenovirus vectors. In: Hames B D, Glover D (eds): DNA Cloning—A practical approach: mammalian systems. Oxford, UK, 1995, p 285–307.
24. Alcorn J L, Gao E, Chen Q, Smith M E, Gerard R D, Mendelson C R. Genomic elements involved in transcriptional regulation of the rabbit surfactant protein-A gene. Mol Endocrinol 1993; 7: 1072–1085.
25. Kopfler W P, Willard M, Betz T, Willard J E, Gerard R D, Meidell R S. Adenovirus-mediated transfer of a gene encoding human apolipoprotein A-Iinto normal mice increases circulating high-density lipoprotein cholesterol. Circulation 1994; 90: 1319–1327.
26. Carmeliet P, Stassen J M, Van Vlaenderen I, Meidell R S, Collen D, Gerard R D. Adenovirus-mediated transfer of tissue-type plasminogen activator augments thrombolysis in tissue-type plasminogen activator-deficient and plasminogen activator inhibitor-1-overexpressing mice. Blood 1997; 90: 1527–1534.
27. Carmeliet P, Moons L, Lijnen R, Janssens S. Lupu F, Collen D, Gerard R D. Inhibitory role of plasminogen activator inhibitor-1 in arterial wound healing and neointima formation. Circulation 1997; 96: 3180–3191.
28. Deutsch D G, Mertz E T. Plasminogen purification from human plasma by affinity chromatography. Science 1970; 170: 1095–1096.
29. Edy J, De Cock F, Collen D. Inhibition of plasmin by normal and antiplasmin-depleted human plasma. *Thromb Res.* 1976; 8: 513–518.
30. Giles A R. Guidelines for the use of animals in biomedical research. Thromb Haemost 1987; 58: 1078–1084.
31. Welsh F A, Sakamoto T, McKee A E, Sims R E. Effect of lactacidosis on pyridine nucleotide stability during ischemia in mouse brain. J Neurochem 1987; 49: 846–851.
32. Bederson J B et al. Evaluation of 2,3,5-triphenyltetrazolium chloride as a stain for detection and quantification of experimental cerebral infarction in rats. Stroke 1986; 17: 472–476.

Present address: E-317, Handa-cho 3776, Hamamatsu, Shizuoka 431-3124, Japan 17

What is claimed is:

1. A method for the treatment of focal cerebral ischemic infarction by adminstering in an effective dosage amount of between about 1.5 to 7.0 mg/kg body weight of at least one $\alpha_2$-antiplasmin neutralizing compound selected from the group consisting of plasmin, mini-plasmin (lacking the first four kringles), and micro-plasmin (lacking all five kringles).

* * * * *

UNITED STATES PATENT AND TRADEMARK OFFICE
CERTIFICATE OF CORRECTION

PATENT NO. : 6,946,438 B1  
DATED : September 20, 2005  
INVENTOR(S) : Nagai et al.

It is certified that error appears in the above-identified patent and that said Letters Patent is hereby corrected as shown below:

<u>Title page,</u>  
Item [73], Assignee, second Assignee should read:  
-- Leuven Research & Development VZW --.  
Item [56], References Cited, OTHER PUBLICATIONS,  
"Skolnick," reference, "in th genomic era" should read -- in the genomic era --.  
"Nagai et al.," reference, "immunoneutralizt6ion reduce focal cerebral schemic" should read -- immunoneutralization reduce focal cerebral ischemic --.  
"Kopler, W.P. et al." reference, "Kopler, W.P. et al. "Adenovirus-mediated transfer of gene" should read -- Kopfler, W.P. et al. "Adenovirus-mediated transfer of a gene --.

Signed and Sealed this

Sixteenth Day of May, 2006

JON W. DUDAS  
*Director of the United States Patent and Trademark Office*